(12) United States Patent
Assaleh et al.

(10) Patent No.: US 7,474,915 B2
(45) Date of Patent: Jan. 6, 2009

(54) SEPARATING MIXED SIGNALS CONTAINING A DISTORTED SIGNAL

(75) Inventors: Khaled Assaleh, Sharjah (AE); Hasan Al-Nashash, Sharjah (AE)

(73) Assignee: American University of Sharjah and Arab Science and Technology Foundation (AE)

( * ) Notice: Subject to any disclaimer, the term of this patent is extended or adjusted under 35 U.S.C. 154(b) by 292 days.

(21) Appl. No.: 11/189,677

(22) Filed: Jul. 26, 2005

(65) Prior Publication Data

US 2007/0027396 A1    Feb. 1, 2007

(51) Int. Cl.
*A61B 5/04* (2006.01)
(52) U.S. Cl. ...................... 600/511; 600/508
(58) Field of Classification Search ................ 600/511, 600/512
See application file for complete search history.

(56) References Cited

U.S. PATENT DOCUMENTS

| | | | |
|---|---|---|---|
| 4,211,237 A * | 7/1980 | Nagel | 600/511 |
| 5,042,499 A | 8/1991 | Frank et al. | |
| 5,123,420 A | 6/1992 | Paret | |
| 5,372,139 A * | 12/1994 | Holls et al. | 600/511 |
| 6,751,498 B1 * | 6/2004 | Greenberg et al. | 600/511 |
| 2007/0066908 A1 * | 3/2007 | Graupe et al. | 600/511 |

* cited by examiner

*Primary Examiner*—Carl H Layno
*Assistant Examiner*—Brian T Gedeon
(74) *Attorney, Agent, or Firm*—Bourque & Associates, PA

(57) ABSTRACT

This invention provides a novel technique separating two mixed signals. The method is particularly useful for fetal electrocardiogram estimation. A maternal electrocardiogram signal recorded at the thorax area is nonlinearly mapped onto an electrocardiogram signal recorded at the abdomen using polynomial networks. The fetal electrocardiogram component is then estimated by subtracting the nonlinearly mapped maternal electrocardiogram signal from the abdominal electrocardiogram signal.

12 Claims, 8 Drawing Sheets

SEPARATING MIXED SIGNALS CONTAINING A DISTORTED SIGNAL

BACKGROUND a. Field of the Invention

This invention relates to a method of separating a signal from a mixture of two signals where a distorted version of one of the signal is available. It is particularly useful for the estimation of a fetal electrocardiogram (FECG) using signals recorded at the surface of the body. The FECG signal reflects the electrical activity of the fetal heart. It contains information on the health status of the fetus and therefore, an early diagnosis of any cardiac defects before delivery increases the effectiveness of the appropriate treatment. There are several technical problems associated with the extraction of FECG from signals recorded at the abdominal surface which result in a poor signal quality. The main sources of possible noise include the maternal ECG, the maternal electromyogram EMG, (50 or 60) Hz power line interference, baseline wandering and random electronic noise. To simplify the problem, it is assumed that state of the art low noise electronic amplifiers with high common mode rejection ratio are used to eliminate the power line interference and electronic random noise. The EMG noise can also be reduced, but not necessarily eliminated, with the use of classical low pass filtering techniques. Therefore, this invention provides a method of suppressing the maternal electrocardiogram (MECG) to extract the FECG.

b. Related Art

The problem of detecting and separating a desired biomedical signal corrupted by other periodic interference and random noise signals is of extreme importance in medicine. Examples include His Purkinje System Electrogram (HPSE) described by H. Al-Nashash, S. Kelly S. and D. Taylor in "Beat-to-Beat detection of His-Purkinje system signals using adaptive filters", Med & Biol. Eng. & Comp., vol. 26, pp. 117-125,1988; and Ventricular Late Potentials (VLP)° and the Diaphragmatic Electromyogram (EMGdi) described by H. Al-Nashash, S. Kelly S. and D. Taylor in "Noninvasive beat-to-beat detection of ventricular late potentials", Med. & Biol. Eng. & Comp., vol. 27, pp. 64-68,1989.

There have been different methods proposed for such extraction including adaptive filters for example in B. Widrow et al., "Adaptive noise canceling: Principle and application," Proc. IEEE, vol. 63, pp. 1692-1716, Dec. 1975 or E. R. Ferrara and B. Widrow, "Fetal electrocardiogram enhancement by time-sequenced adaptive filtering." IEEE Trans Biomed Eng., vol. 29, pp. 451-460, 1982., correlation techniques, for example S. Abbond, A. Alaluf, S. Finav, and D. Sadeh, "Real time abdominal fetal ECG recording using hardware correlator," Comput. Biol. Med., vol. 22, pp. 32-335, 1992, singular-value decomposition (SVD) for example in D. Callaerts, B. D. Moor, J. Vandewalle, and W. Sansen, "Comparison of SVD methods to extract the fetal electrocardiogram from coetaneous electrode signals," Med Biol. Eng. Comput., vol. 28, pp. 217-224, 1990, blind source separation, for example, V. Zarzoso and A. Nandiin "Noninvasive fetal electrocardiogram extraction: Blind separation versus adaptive noise cancellation", IEEE Trans. Biomed Eng., vol. 48, no. 1, pp. 12-18, 2001; or L. De Laflaauwer. B. De Moor and J. Vandewalle, "Fetal Electrocardiograph Extraction by Source Subspace Separation", Proc. IEEE SP/ATHOS Workshop on HOS, Girona, Spain, pp. 134-138, 1995, and wavelet transform, for example, A. Khamene and S. Negahdaripour. "A New Method for the Extraction of Fetal ECG from the Composite Abdominal Signal", IEEE Trans. Biomed. Eng., vol. 47, no. 4, pp. 507-516, 2000 to mention a few. Despite the reported successes of these methods, they are still not used clinically at a large scale.

Other prior art techniques include U.S. Pat. No. 5,042,499 which describes a fetal heart rate monitor which is used to monitor weak fetal electrocardiogram signals in the presence of strong interfering material ECG complexes, general random background muscle noise, and 60 Hz power line noise. This invention uses an electrocardiographic adaptive cancellation process to cancel the maternal ECG component from an abdominal ECG signal recorded from a pregnant subject's abdomen signal.

U.S. Pat. No 5,372,139 describes a method for suppressing a maternal electrocardiogram signal from a fetal electrocardiogram signal obtained with invasive and non-invasive techniques using an almost pure maternal electrocardiogram signal as a trigger. The MECG suppression is achieved by using a substantially pure MECG trace as a trigger signal to calculate an MECG complex template which is subtracted from the composite signal using the MECG trace to align the MECG complex template with each MECG complex (16) in the composite signal.

U.S. Pat. No 6,751,498 describes an apparatus and method for non-invasive, passive fetal heart monitoring. An apparatus and method for fetal heart and maternal heart and uterine monitoring is described which acquires waveforms indicative of the mother's heart beat from sensors located at or near the mother's chest, and waveforms indicative of the combined maternal and fetal heart beats from abdominal sensors located on the mother's abdomen, lower back, or both. The signals from the abdominal sensors are divided into a plurality of channels. An adaptive signal processing filter (ASPF) algorithm or other suitable algorithm is then used to cancel the estimated maternal waveform from each channel derived from the abdominal sensors. The system then selects from the resulting waveforms at least one waveform to serve as the reference fetal waveform. The reference waveform is then processed against the other abdominal waveforms preferably using the ASPF algorithm again to form an enhanced fetal signal that is a representation of the fetus's electrocardiogram.

U.S. Pat. No 5,123,420 describes a method and apparatus for processing heart rate traces in a fetal monitor. A fetal monitor is disclosed which is capable of recording the heart rate trace, preferably the beat-to-beat heart rate trace, of a fetus and a second heart rate trace of the mother or of a second fetus. Coincidence between the heart rate traces is detected by means of a direct or indirect comparison of the two traces and comparison of the difference with a predefined or adaptive limit and a warning signal is generated if coincidence is detected.

SUMMARY OF THE INVENTION

The invention provides an improved method of estimating a desired signal from a first signal and a second signal, where the first signal is a mixed signal considered to comprise the desired signal combined with a distorted version of the second signal, in particular where the desired signal is a fetal electrocardiogram signal, the first signal is an abdominal electrocardiogram signal and the second signal is a thoracic electrocardiogram signal. The abdominal electrocardiogram signal is considered to comprise the fetal electrocardiogram combined with a distorted version of a maternal electrocardiogram signal and the thoracic electrocardiogram signal is assumed to accurately represent the maternal electrocardiogram signal.

The nonlinear distortion which the maternal electrocardiogram signal undergoes is modelled using polynomial networks. An advantage of this approach is that the method is non iterative.

BRIEF DESCRIPTION OF THE DRAWINGS

The invention will now be described, by way of example only with reference to the accompanying drawings: in which.

DETAILED DESCRIPTION

Figure 1:
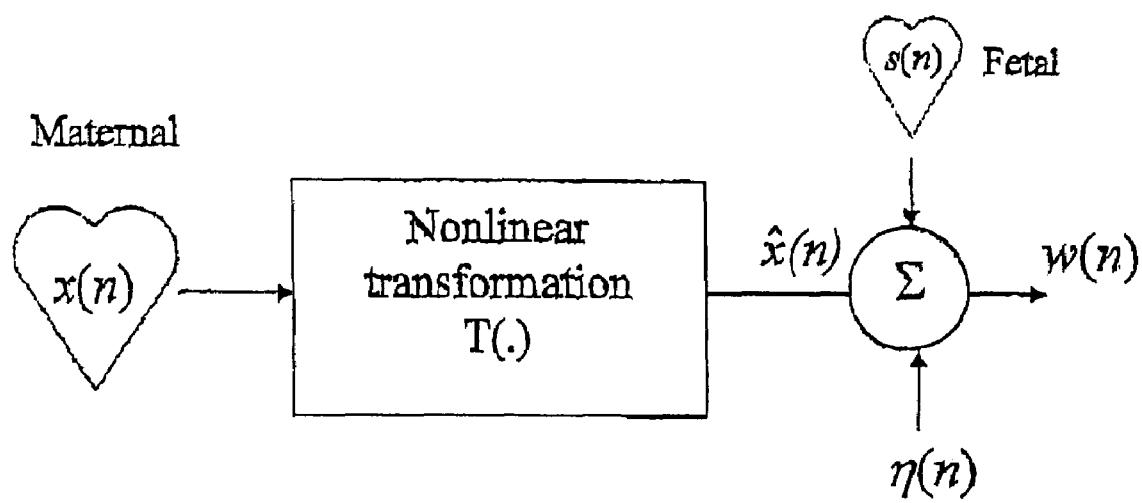
FIG. 1 illustrates schematically an outline of the method of the present invention.

Referring now to FIG. 1, w(n) represents an abdominal ECG signal and x(n) represents a thoracic ECG signal which is assumed to represent accurately the maternal ECG.

The abdominal signal w(n) may be considered to be the sum of a distorted version of the maternal ECG $\hat{x}(n)$ and a noisy version of the fetal ECG $\hat{s}(n)$ such that:

$$w(n) = \hat{x}(n) + \hat{s}(n)$$

$$\hat{s}(n) = s(n) + \eta(n)$$

$\hat{x}(n)$ is distorted due to the fact that the signal is measured far away from its source (the mother's heart), and consequently it encounters some nonlinear transformation as it travels to the abdominal area ie:

$$\hat{x}(n) = T(x(n))$$

The problem would be simple if the transformation T was linear (i.e. if all that x(n) encounters by traveling from the heart to the abdominal areas was time delay and attenuation). In that case, x(n) could be aligned with w(n) via correlation and the signal $\hat{s}(n)$ could be extracted by simply subtracting the aligned x(n) from w(n). Similarly, the problem would be easily solved in the frequency domain by spectral subtraction if the spectra of $\hat{x}(n)$ and $\hat{s}(n)$ were non-overlapping.

Figure 2:
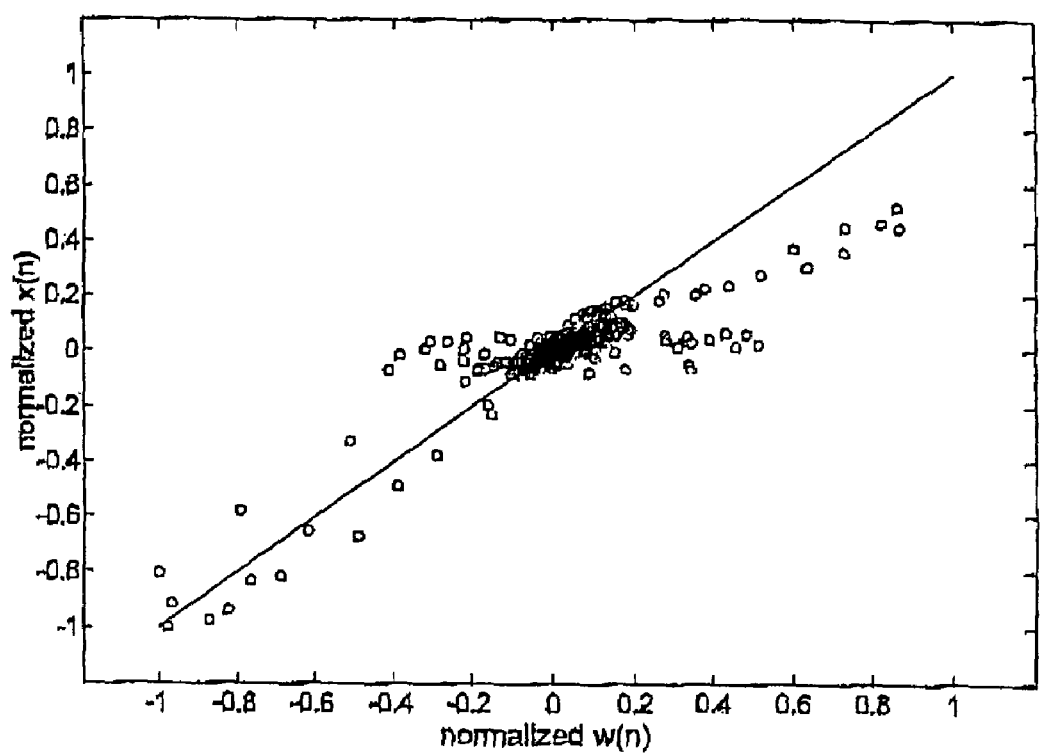
FIG. 2 is a graph illustrating a maternal electrocardiogram signal plotted against an abdominal maternal electrocardiogram signal.

Unfortunately, the transformation between x(n) and the MECG component in w(n) is highly nonlinear as shown in FIG. 2. It can be seen that there is both time warping and time varying scaling. FIG. 2 shows a 360-sample record of normalized w(n) plotted against the corresponding normalized record of x(n). The large values at the extreme right and left of the figure correspond to the MECG peaks, and the scattered values around the horizontal line x(n)=0 and around the region $|w(n)| \in [0.2\ 0.5]$ correspond to the FECG peaks. The nonlinearity of the mapping can easily be seen by the amount of deviation from the unity-slope line. The thoracic signal x(n) is predominantly maternal (MECG), and it is assumed that the fetal component FECG in it is negligible. It should be noted that a proper placement of the thoracic and abdomen electrodes would result in a clean estimate of the FECG such that $\hat{s}(n) \approx s(n)$. If the abdomen electrode is not placed low enough on the mothers abdominal area then the resulting noisy fetal ECG estimate can be cleaned by post filtering using wavelet denoising and/or nonlinear filtering such as median filtering.

In order to estimate $\hat{x}(n)$ and extract s(n) it is necessary to approximate the transformation T. In other words, it is desirable to align x(n) with w(n) in a way where the MECG component is perfectly aligned with x(n). Then the MECG component can be removed from w(n) to leave $\hat{s}(n)$.

The transformation T is generated using polynomial networks which are described in W. M. Campbell, K. T. Assaleh, and C. C. Broun, "Speaker recognition with polynomial classifiers", IEEE Transactions on Speech and Audio Processing, vol. 10, no. 4, pp 205-212, 2002; K. T. Assaleh and W. M. Campbell, "Speaker Identification Using a Polynomial-based Classifier", Proceedings of the fourth international Symposium on Signal processing and its Applications ISSPA '99, Brisbane, Australia, August 1999; and W. M. Campbell and Khaled Assaleh, "Low-Complexity Small-Vocabulary Speech Recognition for Portable Devices", Proceedings of the fourth International Symposium on Signal Processing and its Applications ISSPA '99, Brisbane, Australia, August 1999.

A nonlinear mapping between x(n) and w(n) is determined by minimizing a mean-squared error criterion. This minimization occurs when the dominant component of w(n) (i.e. the MECG) is aligned with x(n).

The method for generating the transformation T is frame-based. The signals x(n) and w(n) are partitioned into contiguous frames of N-samples long.

The $i^{th}$ frames of x(n) and w(n) are given by:

$$x_i(m) = x(iN+m)$$

$$w_i(m) = w(iN+m), \text{ where } 0 \leq m \leq N-1$$

A time derivative vector sequence is generated from the frame $x_i(m)$ and its J time derivatives. Such that (in matrix notation):

$$X_i \begin{bmatrix} x_i(0) & \dot{x}_i(0) & \cdots & x_i^{(J)}(0) \\ x_i(1) & \dot{x}_i(1) & \cdots & x_i^{(J)}(1) \\ \vdots & \vdots & \ddots & \vdots \\ x_i(N-1) & \dot{x}_i(N-1) & \cdots & x_i^{(J)}(N-1) \end{bmatrix}$$

The time derivative vector sequence $X_i$ is then used to generate a Polynomial matrix $P_i$ (comprising a vector sequence $p(x_i(m))$) which is generated by polynomial expansion.

For example, for a two dimensional vector $x_i(m) = [x_i(m)\ \dot{x}_i(m)]$ and a second order polynomial, the vector is given by $$p(x_i(m)) = [1\ x_i(m)\ \dot{x}_i(m)\ x_i(m)\dot{x}_i(m)\ x_i(m)^2\ \dot{x}_i(m)^2]$$

Therefore, by polynomial expansion higher order terms of the vector elements and all possible cross terms with their derivatives are introduced, which allow for highly nonlinear modeling of the problem in hand.

In general, for a $K^{th}$ order polynomial, the polynomial basis terms are monomials of the form $$\prod_{J=0}^{J}(x_i^{(J)}(m))^{k_i}, \text{ where } \sum_{j=0}^{J} k_j \leq K$$

The mapping of the input sequence $x_i(m)$ onto the desired output sequence $w_i(m)$ is achieved by using mean-squared error as the objective criterion such that:

$$c_i = \underset{c_i}{\operatorname{argmin}} \|P_i c_i - w_i\|^2$$

Solving for $c_i$ can be accomplished by applying the method of normal equations as described in B. Noble and 3. W. Daniel, "Applied Linear Algebra", Third Ed., Prentice Hall, 1988 such that $$P_i^t P_i c_i = P_i^t w_i$$

$$c_i = (P_i^t P_i)^{-1} P_i^t w_i$$

The vector $c_i$ maps the input sequence to the output sequence such that the MECG component in $w_i(m)$ is optimally aligned with $x_i(m)$. This mapping is the optimal non-linear approximation of the transformation T in the context of the polynomial networks such that:

$$T(x_i(n)) = \hat{x} \approx P_i c_i$$

Consequently, the FECG component $\hat{s}_i = [\hat{s}_i(0)\ \hat{s}_i(1)\ \ldots\ \hat{s}_i(N-1)]$I the frame $w_i(m)$ can be extracted by subtracting the estimated MECG component from it as follows.

$$\hat{s}_i = w_i - Pc_i$$

Figure 3:
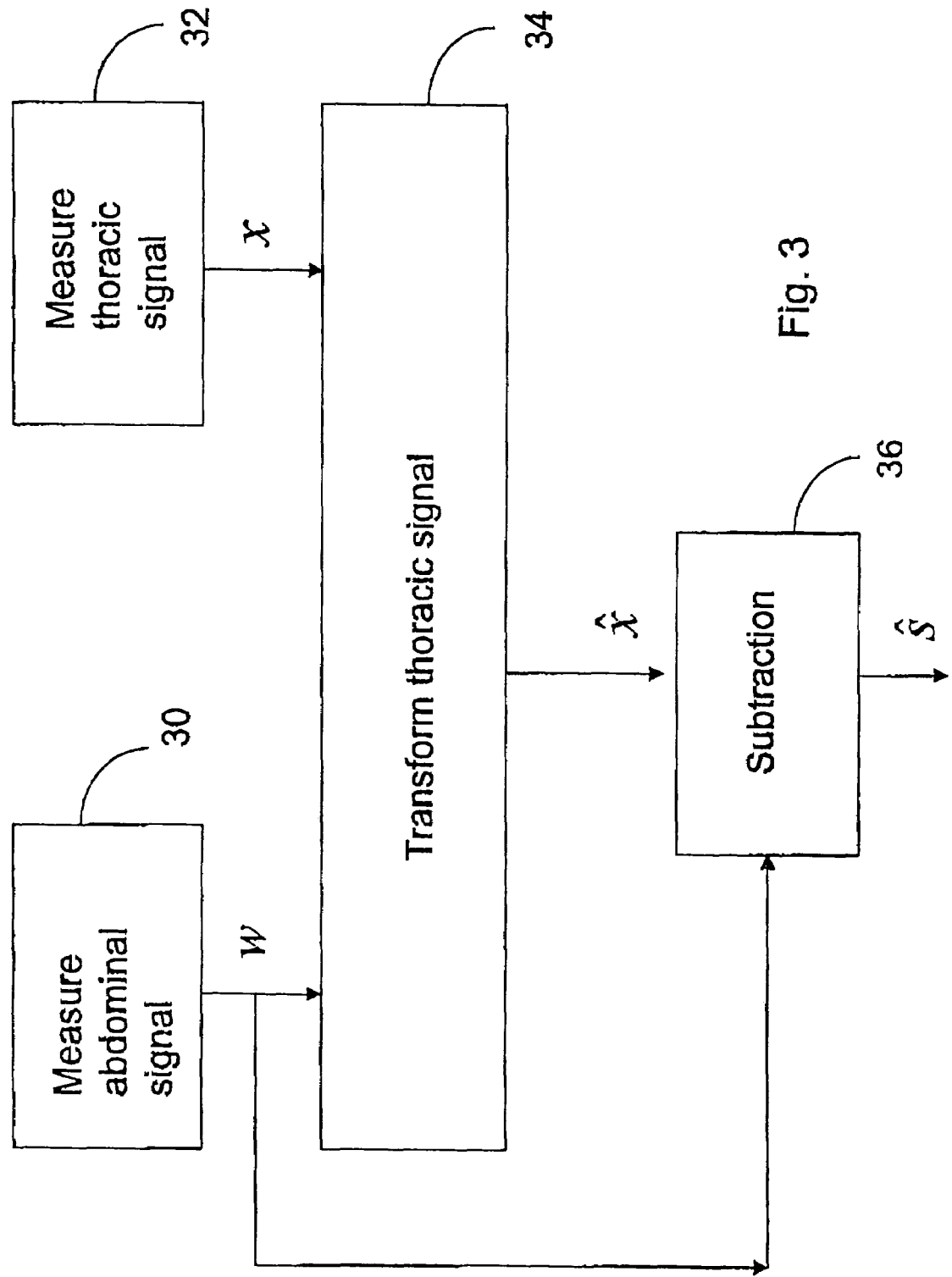
FIG. 3 is a flow chart illustrating the method of the present invention.
Figure 4:
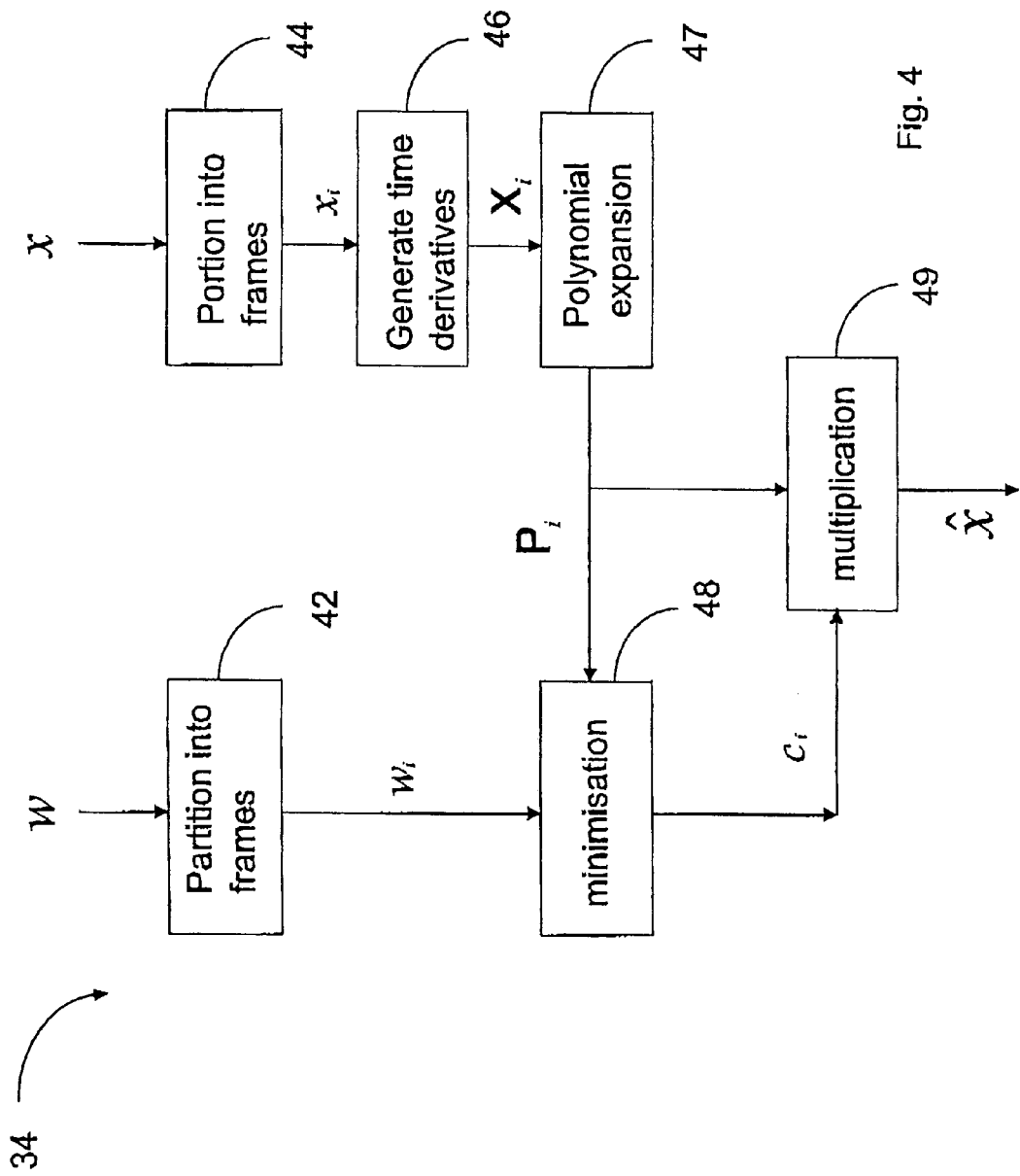
FIG. 4 is a flow chart illustrating the transforming method step in more detail.

FIGS. 3 and 4 are flow charts illustrating the method of the present invention using the principles described above.

Referring to FIG. 3 which shows an overview of the method of the present invention, at step 30 the abdominal electrocardiogram signal w is measured; at step 32 the thoracic electrocardiogram signal x is measured. At step 34 the thoracic electrocardiogram signal is transformed to provided a distorted version of the thoracic electrocardiogram signal $\hat{x}$ such that the difference between the distorted version $\hat{x}$ and the abdominal electrocardiogram signal w is minimised. At step 36 the distorted version of the thoracic electrocardiogram signal $\hat{x}$ is subtracted from the abdominal electrocardiogram signal w to provide an estimate of the fetal electrocardiogram.

The transformation step 34 is described in more detail with reference to FIG. 4. At step 42 the abdominal electrocardiogram signal w is partitioned into a sequence of frames. At step 44 the thoracic electrocardiogram signal x is partitioned into a sequence of frames. Each frame $w_i$ of the abdominal electrocardiogram signal corresponds in time to a frame $x_i$ of the thoracic electrocardiogram signal. In the preferred embodiment of the invention each frame comprises 360 samples of the respective electrocardiogram signal A matrix $X_i$ is then generated from a frame of the thoracic electrocardiogram signal $x_i$. In the preferred embodiment of the invention 3 time derivatives are used, thus the matrix $X_i$ has is 360×4 values.

Polynomial expansion is than applied to the matrix $X_i$ at step 47 to create a polynomial matrix $P_i$. In the preferred embodiment of the invention a third order polynomial expansion is used and hence $P_i$ has the dimensions 360×35.

At step 48 the polynomial matrix $P_i$ is used together with the corresponding frame of the abdominal electrocardiogram signal $w_i$ to generate a vector $c_i$ in accordance with the equation $c_i = (P_i^t P_i)^{-1} P_i^t w_i$ as described above. It wil be appreciated that in the preferred embodiment of the Invention $(P_i^t P_i)^{-1}$ has the dimensions 35×35.

Vector $c_i$ is then multiplied by the polynomial matrix $P_i$ at step 49 to produce the required distorted version of the thoracic electrocardiogram signal $\hat{x}$.

Figure 5:
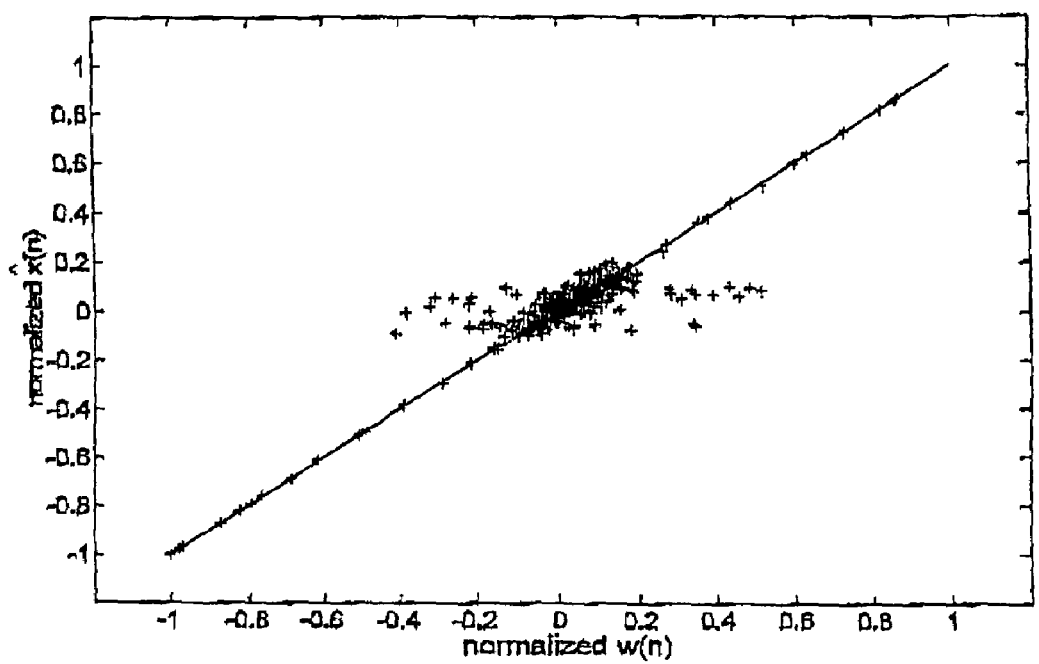
FIG. 5 is a graph illustrating a transformed maternal electrocardiogram signal plotted against an abdominal maternal electrocardiogram signal.

FIGS. 5 shows a graph of w(n) against the separated MECG component $\hat{x}(n)$. The larger values of both signals are perfectly aligned do it is possible to subtract the MECG component from w(n).

Figure 6:
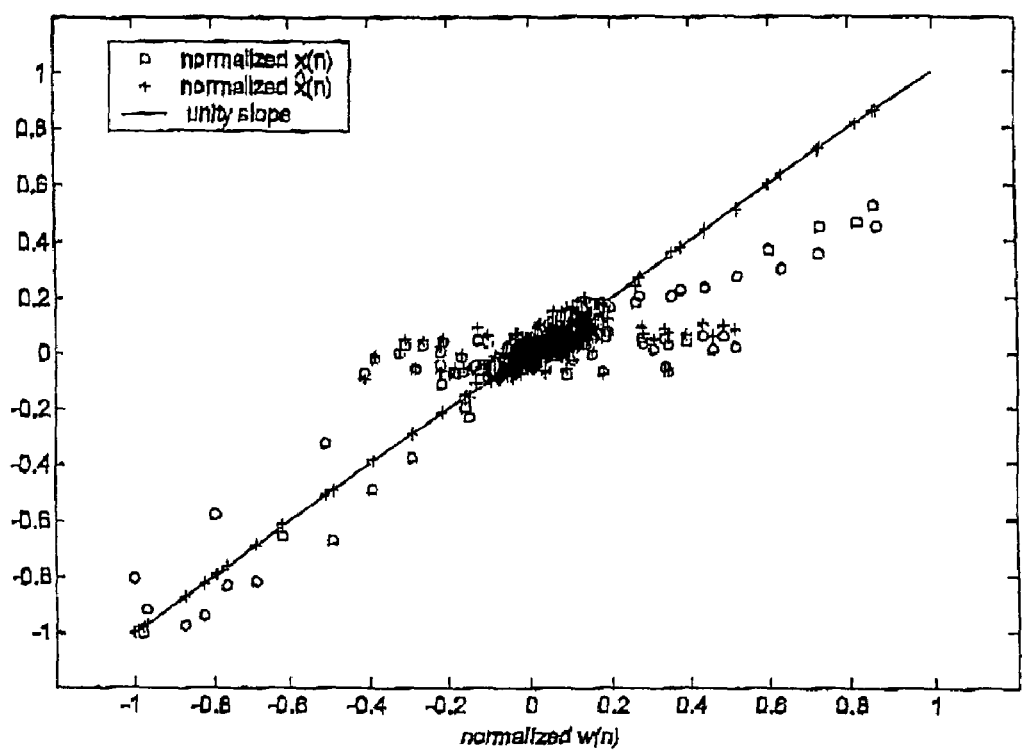
FIG. 6 is a graph comparing the plots shown in FIG. 4 and FIG. 2.

FIG. 6 show the graph of FIG. 5 superimposed upon the graph of FIG. 2 to illustrate alignment before and after the transformation. It will be appreciated that that the MECG component in w(n) is aligned while the FECG component is almost unchanged.

Figure 7:
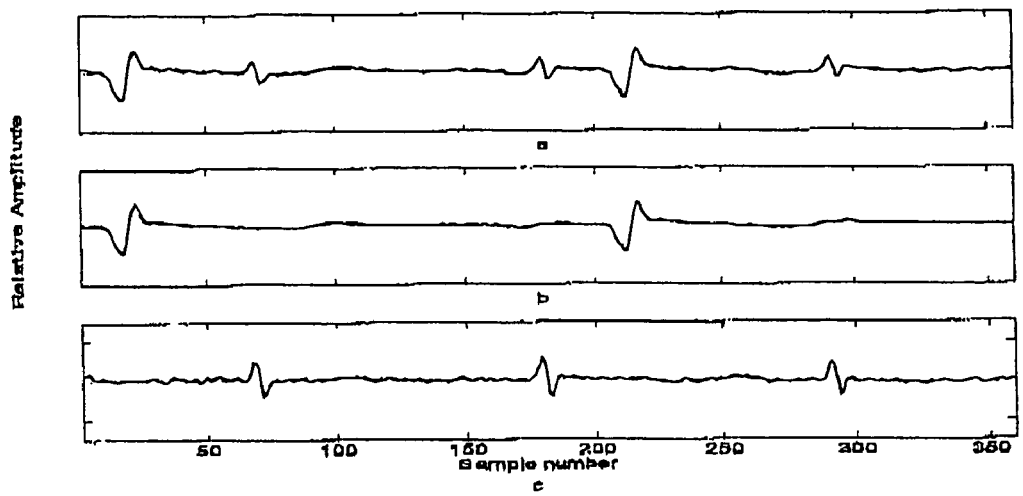
FIGS. 7, 8 and 9 illustrate results of applying the method of the invention to various pair of signals
Figure 8:
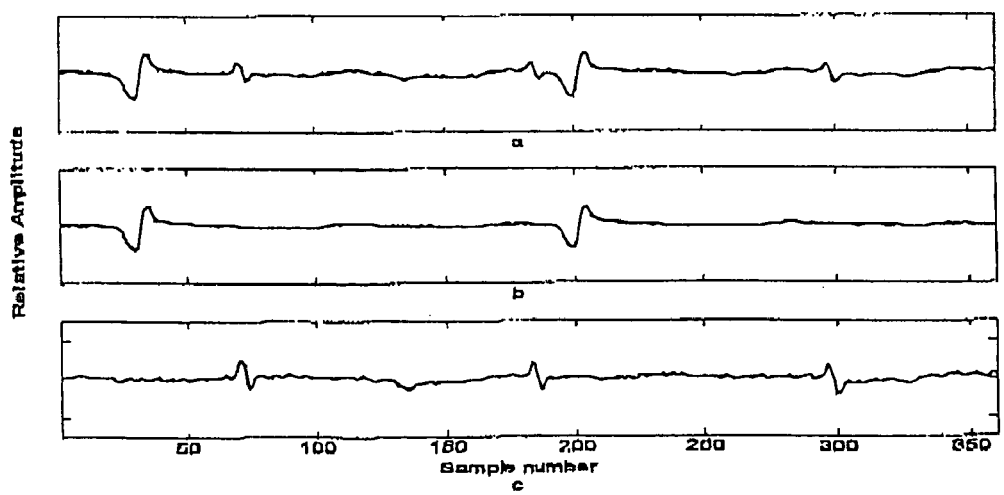
Figure 9:
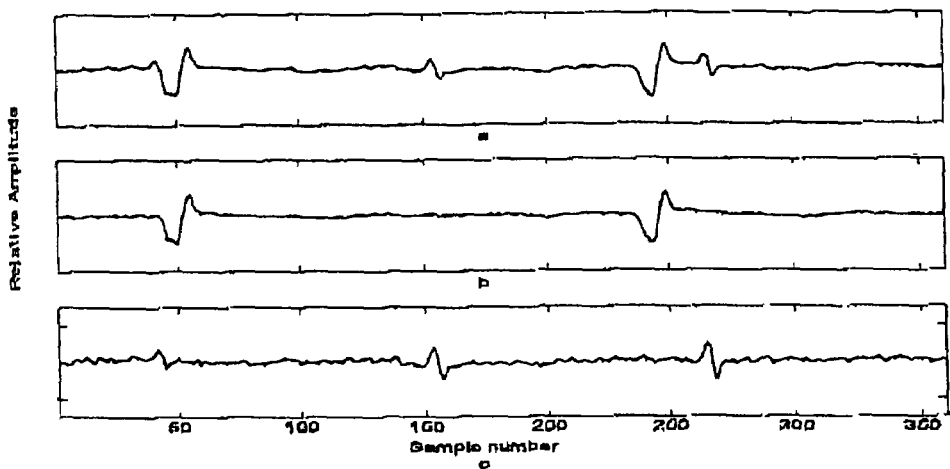

FIGS. 7, 8 and 9 show how the proposed technique extracts the FECG component from w(n) for three representative frames.

FIG. 7.a shows one frame of w(n) containing non-overlapping 3 FECG beats and two MECG beats. FIG. 7.b shows the output x(n)of the nonlinear mapping process as described above. FIG. 7.c depicts the extracted FECG signal which clearly shows the separated 3 beats while completely eliminating the presence of the MECG in w(n).

FIG. 8.a, b shows another frame of w(n) containing a partial overlap between one of the FECG beats with one MECG beat, and the corresponding frame of $\hat{x}(n)$. FIG. 7.c depicts the extracted FECG signal which clearly shows the separated 3 beats while completely eliminating the presence of the MECG in w(n).

To demonstrate the power of the method of the invention in extracting the FECG, FIG. 9.a shows a third frame of w(n) containing full overlap between the first FECG and the MECG beats. This case represents the extreme case where the FECG is completely dominated by the MECG component to the point that the FECG beat is no longer visually distinguishable. FIG. 9.c shows that the algorithm was still successfully capable of extracting the FECG signal.

Independent component analysis (ICA) technique has been successfully used by several research groups for the extraction of FECG. See, for example, V. Zarzoso and A. Nandi, "Noninvasive fetal electrocardiogram extraction: Blind separation versus adaptive noise cancellation", IEEE Trans. Biomed Eng., vol. 48, no, I, pp. 12-18, 2001. and B. Widrow et al., "Adaptive noise canceling: Principle and application," Proc. IEEE, vol. 63, pp. 1692-1716, December 1975.

However, multiple leads were required for successful separation of the FECG. In practice and for monitoring purposes, it is highly desirable that the FECG is extracted using fewer leads. As illustrated in FIGS. 7-9, the method of the invention is capable of extracting FECG using two leads only. However, this is not possible with the ICA method described by Zaroso and Nandi.

Figure 10:
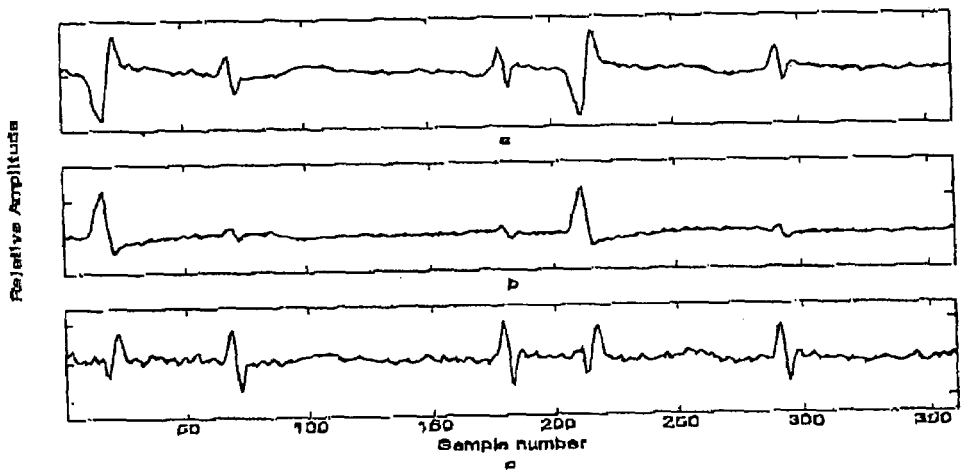
FIG. 10 illustrates the result of applying a prior art technique to the signals of FIG. 7.

FIG. 10.a shows one frame of w(n) containing non-overlapping three FECG beats and two MECG beats (same as in FIG. 7.a). FIGS. 10b, and 10c show the output of the ICA separated MECG and FECG respectively using two channels only. Clearly, the generated outputs are still composite, and a strong component of the MECG is still apparent in the extracted FECG.

It is to be recognized that various alterations, modifications, and/or additions may be introduced into the method described above without departing from the spirit or ambit of the present invention.

The invention claimed is:

1. A method of estimating a fetal electrocardiogram signal comprising the steps of:
   measuring an abdominal electrocardiogram signal from the abdomen of a pregnant female;
   measuring a thoracic electrocardiogram signal from the thorax of said pregnant female;
   transforming the thoracic electrocardiogram signal using a polynomial network to provide a transformed thoracic electrocardiogram signal such that the difference between the transformed thoracic electrocardiogram signal and the abdominal electrocardiogram signal is minimised; and subtracting the transformed thoracic electrocardiogram signal from the abdominal electrocardiogram signal to provide an estimated fetal electrocardiogram signal, wherein the transforming step comprises the sub-steps of:
   partitioning the thoracic electrocardiogram signal into a plurality of frames comprising a plurality of signal samples;
   generating a time derivative vector sequence comprising a frame of the thoracic electrocardiogram signal and one or more time derivatives of said frame;
   generating a polynomial matrix for said frame said matrix comprising a vector sequence of polynomial basis terms in dependence upon said time derivative vector sequence;
   partitioning the abdominal electrocardiogram signal into a plurality of frames each frame corresponding in time with a frame of the thoracic electrocardiogram signal;
   generating a mapping vector in dependence upon said polynomial matrix for said frame and upon a corresponding frame of the abdominal electrocardiogram signal; and
   generating the transformed thoracic electrocardiogram signal in dependence upon said mapping vector and said polynomial matrix.

2. A method according to claim 1, in which the step of generating the mapping vector comprises the sub-steps of:
   multiplying the transform of the polynomial matrix by the polynomial matrix itself;
   generating the inverse of the multiplied result;
   multiplying the inverse by the polynomial matrix; and
   multiplying the result by said frame of the abdominal electrocardiogram signal.

3. A method according to claim 1, in which each frame comprises 360 samples.

4. A method according to claim 1 in which the number of time derivatives is equal to three.

5. A method according to claim 1 in which the polynomial basis terms are generated using a third order polynomial.

6. A method of estimating a fetal electrocardiogram signal comprising the steps of:
   measuring an abdominal electrocardiogram signal from the abdomen of a pregnant female;
   measuring a thoracic electrocardiogram signal from the thorax of said pregnant female;
   transforming the thoracic electrocardiogram signal using a polynomial network to provide a transformed thoracic electrocardiogram signal is minimised;
   subtracting the transformed thoracic electrocardiogram signal from the abdominal electrocardiogram signal to provide an estimated fetal electrocardiogram signal;
in which the transforming step comprises the sub-steps of:
   partitioning the thoracic electrocardiogram signal into a plurality of frames comprising a plurality of signal samples;
   generating a time derivative vector sequence comprising a frame of the thoracic electrocardiogram signal and one or more time derivatives of said frame;
   generating a polynomial matrix for said frame said matrix comprising a vector sequence of polynomial basis terms in dependence upon said time derivative vector sequence;
   partitioning the abdominal electrocardiogram signal into a plurality of frames each frame corresponding in time with a frame of the thoracic electrocardiogram signal;
   generating a mapping vector in dependence upon said polynomial matrix for said frame and upon a corresponding frame of the abdominal electrocardiogram signal; and
   generating the transformed thoracic electrocardiogram signal in dependence upon said mapping vector and said polynomial matrix.

7. A method according to claim 6, in which the step of generating the mapping vector comprises the sub-steps of:
   multiplying the transform of the polynomial matrix by the polynomial matrix itself;
   generating the inverse of the multiplied result;
   multiplying the inverse by the polynomial matrix; and
   multiplying the result by said frame of the abdominal electrocardiogram signal.

8. A method according to claim 6, in which each frame comprises 360 samples.

9. A method according to claim 6, in which the transforming step includes the sub-step of generating time derivatives of the thoracic electrocardiogram signal.

10. A method according to claim 9, in which said polynomial network is based on said time derivatives.

11. A method according to claim 9 in which the number of time derivatives is equal to three.

12. A method according to claim 6 in which the polynomial basis terms are generated using a third order polynomial.

* * * * *